United States Patent [19]

Kuehne et al.

[11] Patent Number: 4,886,602
[45] Date of Patent: Dec. 12, 1989

[54] PROCESS FOR THE SEPARATION OF BIOTECHNOLOGICALLY PRODUCED VALUABLE MATERIALS FROM A FERMENTER BROTH BY CROSSFLOW MICRO- AND/OR ULTRAFILTRATION

[75] Inventors: Norbert Kuehne, Haan; Wilfried Raehse, Duesseldorf; Franz-Josef Carduck, Haan, all of Fed. Rep. of Germany

[73] Assignee: Henkel Kommanditgesellschaft auf Aktien, Duesseldorf, Fed. Rep. of Germany

[21] Appl. No.: 245,101

[22] Filed: Sep. 15, 1988

[30] Foreign Application Priority Data

Sep. 15, 1987 [DE] Fed. Rep. of Germany ....... 3730868

[51] Int. Cl.$^4$ ............................................. B01D 13/00
[52] U.S. Cl. .................................... 210/637; 210/641; 210/644; 210/645; 210/651; 210/653
[58] Field of Search ........ 210/634, 637, 641, 644–647, 210/649–653

[56] References Cited

U.S. PATENT DOCUMENTS 4,751,003  6/1988  Raehse et al. ........................ 210/641

FOREIGN PATENT DOCUMENTS 3515650  11/1986  Fed. Rep. of Germany .

Primary Examiner—Frank Sever
Attorney, Agent, or Firm—Ernest G. Szoke; Wayne C. Jaeschke; Daniel S. Ortiz

[57] ABSTRACT

The invention is a process for the separation of biotechnologically produced valuable materials from a fermenter broth by crossflow microfiltration and/or ultrafiltration, in which at least two modules arranged in series and fitted with porous membranes are used per stage, to produce concentrate and a permeate which contains the valuable material. The pressure of the permeate is controlled so that the absolute pressure on the permeate side is at different absolute pressure in each module.

9 Claims, 1 Drawing Sheet

PROCESS FOR THE SEPARATION OF BIOTECHNOLOGICALLY PRODUCED VALUABLE MATERIALS FROM A FERMENTER BROTH BY CROSSFLOW MICRO- AND/OR ULTRAFILTRATION

BACKGROUND OF THE INVENTION

1. Field of the Invention

This invention is a process for the separation of biotechnologically produced valuable materials from a fermenter broth by crossflow microfiltration and/or ultrafiltration, in which at least two modules arranged in series and fitted with porous membranes are used per stage.

2. Statement of Related Art

Processes such as these for the recovery of valuable materials from fermenter solutions are known. In crossflow membrane microfiltration, the dissolved valuable material is separated from the fermenter broth as permeate. The valuable material is then concentrated in another unit, for example by precipitation or by ultrafiltration or reverse osmosis. Both microfiltration with pore diameters of 0.02 to 10 $\mu$m and ultrafiltration with pore diameters of 0.001 to 0.02 $\mu$m are carried out in modules arranged in series. A sufficiently high pressure has to be applied to the fermenter broth entering the first module to ensure that, due to the pressure losses occurring in the modules, a sufficiently large transmembranal pressure difference for separation is provided in the last module.

The disadvantage of the known processes lies in the problem of concentration polarization which always arises in membrane processes. In microfiltration, due to the flux of materials onto the membrane surface, the valuable materials arrive at the pores of the membrane, along with materials which are unable to pass through the pores because of their size. A surface layer of complex composition is thus formed on the membrane surface and obstructs the flow of material, particularly the valuable material, through the membrane during the concentration phase. Retention (of the valuable materials) is thus increased and permeate flux reduced. To maintain the separation efficiency of the process, the concentration phase has to be terminated at a relatively low degree of concentration and the membrane surfaces have to be cleaned.

Applicants' patent No. DE 35 15 650 describes a process which largely obviates this disadvantage. However, this process is based on the use of certain membrane materials and precisely defined hydrodynamic conditions. Accordingly, this process is only suitable for certain biotechnology products.

Accordingly, an object of the present invention is to provide a microfiltration process which provides for minimal retention of the valuable material despite high permeate flux and which can be universally applied.

BRIEF DESCRIPTION OF THE INVENTION

According to the invention, a process is provided whereby minimal retention of the valuable material occurs at high permeate flux wherein a different pressure in relation to the ambient pressure is maintained on the permeate in each module.

In the process of the invention, a valuable material (biologically produced) is separated from a fermenter broth by being passed over a microfiltration or ultrafiltration member. In microfiltration, the valuable material is recovered in a permeate. In ultrafiltration the valuable material is recovered in the concentrate. Whenever the microfiltration or ultrafiltration member are arrange in at least two modules which modules communicate in series to receive the fermenter broth, the pressure of the permeate is controlled so that the permeate pressure in each module is different in relation to ambient pressure.

DETAILED DESCRIPTION OF THE INVENTION

Figure 1:
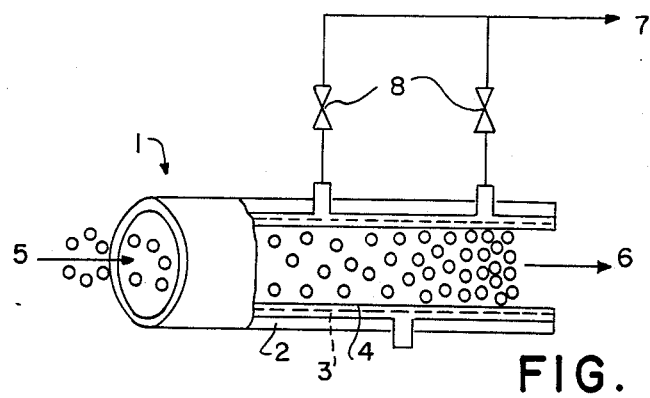
FIG. 1 shows the principle of crossflow membrane filtration of the separation of valuable materials from culture or fermenter solutions.

It has been found that the retention of the valuable material and the permeate flux are dependent on the mean transmembranal pressure difference. As used herein mean transmembranal pressure difference is the arithmetic mean of input and output pressure difference across a membrane in a module. The average pressure of a module is the arithmetic mean between the inlet and outlet pressure. As the mean transmembranal pressure difference increases, permeate flux increases rapidly at first and then reaches a limit. By contrast, in microfiltration retention of the valuable material increases with increasing pressure difference. According to the invention, the pressure on the permeate in relation to the ambient pressure is controlled to obtain an optimal transmembranal pressure difference in all successive modules to which different pressures are applied on the concentrate side. The optimum pressure difference can thus be established in each module. Retention reaches its minimal value while permeate flux is high enough to enable the process to be carried out economically.

In an embodiment of the invention, the pressure on the permeate side is controlled so that the pressure on the permeate side of the module is reduced from the input module to the output module in such a way that a substantially equal mean transmembranal pressure difference between concentrate and permeate is applied in all the modules.

In view of the pressure losses in the modules, the entry pressure into the first module on the concentrate side is considerably higher than the exit pressure from the last module in a series. In conventional membrane separation processes, therefore, the transmembranal pressure difference is reduced from module to module. Accordingly, the transmembranal pressure difference is so high, at least in the first module, that the retention of the valuable material is high. By contrast, according to the present invention, a constant or optimal transmembranal pressure difference is established in all modules, guaranteeing constant, low retention.

According to the invention, the pressure can be controlled below ambient pressure on the permeate side of one or more modules at the end of a series of modules. Depending on the particular application, it is preferred to apply a reduced pressure on the permeate side of the last stage in order to obtain a uniform or optimum transmembranal pressure difference in all the modules.

In another embodiment of the invention, microfiltration is carried out at flow velocities higher than 4 (meters/second) and, more particularly, in the range from 5 to 7 m/s. It has been found that these flow velocities are particularly favorable.

In another embodiment, inorganic materials, such as aluminium oxide, silicon carbide or zirconium dioxide on a support, are used as the filtration member materials. These membranes have the advantage that they can be sterilized by treatment with steam, no membrane compaction occurs and the membranes are not subjected to abrasion. However, corresponding organic membranes may also be used in accordance with the invention.

Another preferred embodiment of the invention in which microfiltration is used in conjunction with ultrafiltration, the permeate from the ultrafiltration is mixed with the fermenter broth feed to dilute the fermenter broth and as a diallization liquid. A salt solution may also be used.

The invention is described in more detail in the following with reference to the accompanying diagrammatic drawings, wherein:

A tubular separation module 1 as used in the process is illustrated in principle in FIG. 1 for the separation of biotechnology produced valuable materials from a cell suspension (fermenter broth, optionally after cell disintegration) by crossflow membrane filtration. The separation module 1 consists of a support tube 2 in which is arranged a carrier tube 3 to the inner surface of which a separation active membrane layer 4 is applied. In the embodiment illustrated by way of example, the tubular separation module 1 has a length of approximately 1.2 m. If the carrier tubes are stable, there is no need for the support tube 2.

The culture or fermenter mixture 5 is passed over the separation-active membrane layer 4 in the arrowed direction at flow velocities of approximately 5–7 m/s, the valuable materials passing radially through the membrane layer 4 while cells, cell fragments and solids are retained by the membrane layer 4.

A liquid concentrate 6 containing the cells, cell fragments and solids and a liquid permeate 7 containing the valuable material are formed. The driving force for the separation of concentrate 6 and permeate 7 is a transmembranal pressure difference. This transmembranal pressure difference is established through a higher pressure on the concentrate side in relation to the permeate side. In order to be able to apply a uniform or optimal transmembranal pressure difference in all of the modules 1, a predetermined pressure is established on the permeate side, by passing the permeate through flow restrictors 8 to discharge the permeate 7.

Figure 2:
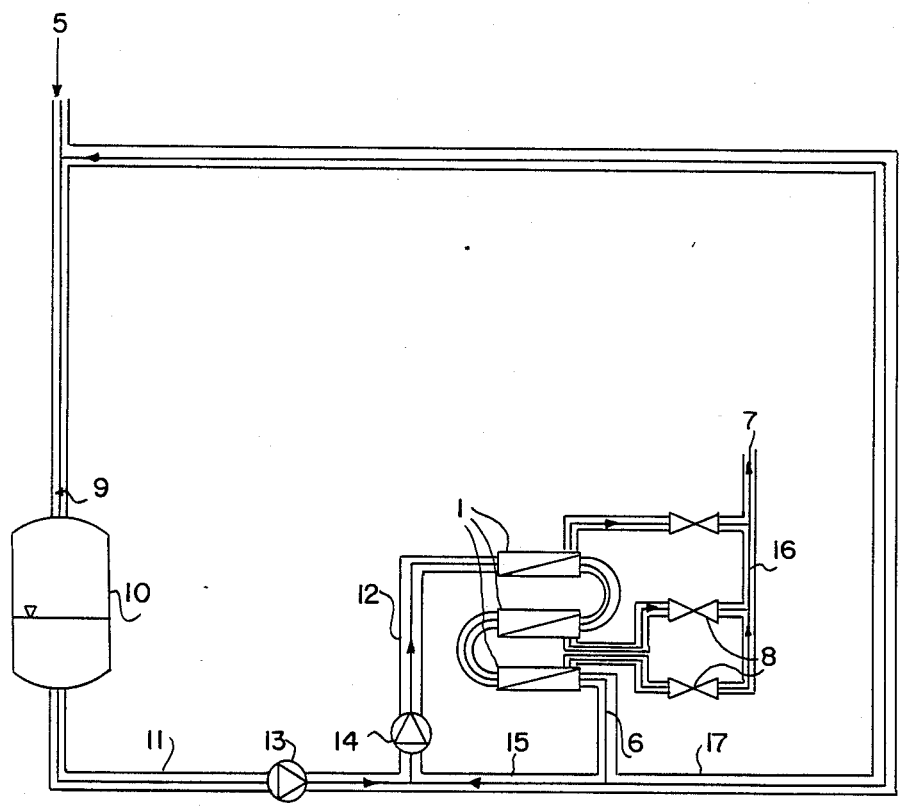
FIG. 2 is a simplified process diagram of a crossflow membrane filtration plant for carrying out a microfiltration process according to the invention.

The tubular separation modules 1 are the separation means of the simplified flow diagram of a crossflow microfiltration plant shown in FIG. 2. The fermenter solution 5 is introduced through a pipe 9 into a temperature-controlled holding vessel 10 or is taken directly from the fermenter from which it enters the tubular separation modules 1 through pipes 11, 12 by means of a feed pump 13 in the pipe 11 and a circulation pump 14 in the pipe 12. In this case, three series arranged separation modules 1 form one stage. In each of the three tubular separation modules 1, the culture or fermenter solution 1 is separated into a concentrate 6 and a permeate 7, the concentrate 6 passing through pipes into the next module 1 or being for the most part recycled from the last module through pipes 6 and 15 by the circulation pump 14 while the permeate 7 flows from each separation module 1 into an outflow pipe 16. In the case of batch operation, a relatively small part of the concentrate 6 passes back into the vessel 10 or fermenter through a branch pipe 17 and the pipe 9. In continuous operation, the concentrate 6 is taken directly from the pipe 17. FIG. 2 shows a single-stage construction of the separation plant. In practice, up to ten separation stages are normally used.

In one typical embodiment of the invention, three modules 1 each 1.2 m in length are arranged in series and operated in such a way that the exit pressure of the first module on the concentrate side corresponds to the entry pressure of the second module, etc. The pressure drop per module is 1.8 bar, i.e. in all 5.4 bar. The fermenter composition 5 enters the first module 1 at an entry pressure of 6.1 bar in relation to the ambient pressure. The exit pressure in the last module is thus 0.7 bar gauge. To obtain a uniform mean transmembranal pressure difference in each stage, a decreasing pressure, in relation to the ambient pressure, is applied from stage to stage on the permeate side 7. The pressure on the permeate side measures 3.6 bar in the first module, 1.8 bar in the second module and 0 bar in the third module. A constant mean transmembranal pressure difference of 1.6 bar is thus obtained in every stage. The permeate 7 pressure is reduced by the flow restrictions 8 before entering the outflow pipe 16. The process principle may be applied to any number of successive modules from two modules upwards.

In an other embodiment, the permeate 7 flows through the outflow pipe 16 into a separation stage, for example a precipitation stage or an ultrafiltration unit, for concentration of the valuable materials. If necessary, the ultrafiltration unit may also be operated by the same counter-pressure technique as applied in crossflow microfiltration, i.e. with application of a stagedependent pressure on the permeate side.

The permeate from the ultrafiltration may also be used to dilute the fermenter broth and as diallization liquid. Good results have also been obtained through preliminary dilution and diallization with salt solutions, particularly of salts which stabilize the proteins.

The process is also suitable for the recovery of valuable materials when they are not secreted into the fermentation medium from the microorganisms producing them, but instead can only be recovered after destruction of the cells by mechanical or chemical (enzymatic) means.

The invention is not limited to the embodiments illustrated by way of example in the accompanying drawing. The modules may be differently constructed, for example as plate modules or as multichannel units, and may be differently subdivided in length, and the like.

We claim:

1. A process for the separation of valuable biologically produced compositions from a fermenter broth which comprises: providing universally applicable maximal recovery of said compositions under high flux by passing the fermenter broth through at least two modules which can be microfiltration or ultrafiltration separation modules arranged in series wherein the fermenter broth, at a first pressure, contacts a separation membrane in the first module to produce a concentrate and a permeate in the first module, the permeate is produced at a pressure lower than the first pressure, and the fermenter broth is passed through each succeeding module in the series at a pressure lower than the pressure in the preceeding module to produce a permeate at a pressure lower than the pressure in the module and controlling the pressure of the permeate in each module so that the permeate absolute pressure in each module is different.

2. A process of claim 1, wherein permeate pressure in each module is reduced from the input module to the output module in such a way that a mean transmembranal pressure difference between the concentrate (6) and the permeate (7) is substantially equal in all the modules (1).

3. A process of claim 1 wherein the pressure of the permeate is controlled below ambient pressure in the last module.

4. A process of claim 1 wherein a microfiltration is carried out at flow velocity higher than about 4 m/s.

5. A process of claim 4 wherein the flow velocity is from about 5 to about 7 m/s.

6. A process of claim 1 wherein the membrane material comprises at least one material selected from aluminium oxide, silicon carbide or zirconium dioxide on a support.

7. A process of claim 1 carried out under sterile conditions with recycling of the concentrate to dilute the fermenter broth.

8. A process of claim 1 comprising a microfiltration followed by an ultrafiltration wherein the permeate from the ultrafiltration is used in the microfiltration to dilute the fermenter broth and also as a diallizing liquid.

9. A process of claim 1, wherein in microfiltration, a salt solution is used to dilute the fermenter broth and also as a diallization liquid.

* * * * *